United States Patent [19]

Mulder

[11] Patent Number: 5,700,242
[45] Date of Patent: Dec. 23, 1997

[54] BALLOON CATHETER AND METHOD FOR FACILITATING INCREASED RADIAL EXPANSION

[75] Inventor: Hugo Mulder, Groningen, Netherlands

[73] Assignee: Cordis Corporation, Miami Lakes, Fla.

[21] Appl. No.: 562,307

[22] Filed: Nov. 22, 1995

[30] Foreign Application Priority Data

Nov. 22, 1994 [NL] Netherlands ............................ 9401951

[51] Int. Cl.[6] .................................................. A61M 29/00
[52] U.S. Cl. .............................................. 604/96; 606/194
[58] Field of Search ..................... 604/96–105, 246–250; 606/192, 194

[56] References Cited

FOREIGN PATENT DOCUMENTS 2020557  11/1979  United Kingdom.
8303204   9/1983  WIPO.

Primary Examiner—Corrine M. McDermott
Assistant Examiner—Deborah Blyveis
Attorney, Agent, or Firm—Michael W. Montgomery

[57] ABSTRACT

A balloon catheter incorporates a tubular shaft which defines an inflation lumen communicating with a flexible, relatively inelastic balloon. The balloon catheter is constructed to allow the proximal and distal ends of the balloon to shift toward each other during inflation, thereby allowing the balloon to exhibit increased radial expansion.

14 Claims, 1 Drawing Sheet

BALLOON CATHETER AND METHOD FOR FACILITATING INCREASED RADIAL EXPANSION

BACKGROUND AND DESCRIPTION OF THE INVENTION

The present invention relates generally to medical catheters, and more specifically to a balloon catheter having a balloon capable of increased radial expansion.

Medical catheters of different types are used for a variety of purposes, including radiology, esophageal procedures, peripheral angioplasty, and angiography. Medical catheters generally have a proximal hub, a body, and a distal tip portion. The body is formed of a flexible, relatively narrow tubular material having sufficient length to traverse a path from an external incision to an internal region of interest within the body of the patient. The proximal hub enables the catheter to be coupled with medical equipment which is used to perform a medical procedure at the distal tip portion. In a typical medical procedure such as radiology angiography or angioplasty, the catheter is usually pre-loaded onto a guidewire by feeding the guidewire through the catheter until a relatively short distal portion of guidewire extends distally beyond the tip of the catheter, with a portion of the guidewire extending proximally from the catheter hub. The pre-loaded catheter and guidewire are then inserted into the body of the patient, steering them into the proper passageways, until the tip of the guidewire is disposed in the desired region.

In the particular example of balloon angioplasty, a guiding catheter may be initially placed through the large access artery or vessel, and its tip is disposed near to the desired site. The guiding catheter thus acts as a conduit to access the various blood vessels with a guidewire and subsequently a balloon catheter. The guiding catheter is constructed of plastic tubing approximately one meter in length, and has a inside diameter substantially within the range of 5 to 14 French size. The term "French size" is defined as an object having a major dimension of a multiple of 0.013 inches or 0.33 millimeters.

Balloon angioplasty catheters and other associated apparatus are described in U.S. Pat. No. 4,906,244 to Pinchuk et al. entitled, "Balloons For Medical Devices And Fabrication Thereof," and U.S. Pat. No. 5,370,615 to Johnson entitled, "Balloon Catheter For Angioplasty," the disclosures of which are incorporated herein by reference. A balloon catheter is an elongated flexible plastic shaft having a balloon at the distal end of the catheter shaft, and this balloon can be expanded by supplying inflation fluid under pressure through a passage, or lumen, in the catheter shaft. Both ends of the balloon member are connected with the catheter shaft in a sealed manner. The volume enclosed by the balloon in between these sealed connections, at least one opening is arranged in catheter shaft in order to supply the inflation fluid under pressure from the lumen to the inside of the balloon, and also to subsequently remove the inflation fluid from the balloon for withdrawal through the guiding catheter.

A balloon catheter may be designed with an integral "fixed-wire" at its distal end, or may be used with a guidewire in an "over-the-wire" technique. An over-the-wire balloon catheter has at least two longitudinal passages, or lumens, and a substantially inelastic balloon located near its distal tip. One lumen slidingly accepts the guidewire, while the other lumen allows communication of inflation fluid from the proximal hub to the interior of the balloon to inflate it at pressures which usually range from four to twelve atmospheres, to conduct the angioplasty.

The guidewire and balloon catheter may be inserted through the guiding or other vascular insertion device catheter until the balloon is near the distal end of the guiding catheter. Then the balloon catheter and guidewire tip are manipulated to advance them into the vascular. When the balloon is located in a restricted region of the artery, inflation fluid is injected through the inflation lumen, causing the balloon to inflate and reopen the artery 18 as shown in FIG. 2, to allow sufficient blood flow.

It is desirable to provide a balloon catheter having the smallest possible cross-section, or profile, when the balloon is deflated. In the case of angioplasty catheters, the profile should be as small as possible to enable the catheter to navigate the relatively small and tortuous coronary arteries and to cross restricted or blocked vessels, referred to as lesions. Indeed, the profile must be smaller than a maximum limit imposed by the fact that the catheter and deflated balloon must fit through a vascular insertion device and be inserted percutaneously.

Conversely, it is also desirable in many cases to provide the largest possible inflated cross-section or effective diameter, to treat larger blood vessels or other body passages. However, given the maximum deflated profile and the thickness of the balloon material, only a certain amount of the balloon material may be used. In addition, the balloon material is preferably inelastic for proper therapeutic effect, so a certain maximum inflated diameter can be calculated. Beyond this maximum diameter, the expansion possibilities of the balloon are limited because any further expansion in the radial direction must be accompanied by a reduction or shortening in the axial direction. Because the ends of the balloon are fixed to the catheter shaft, existing balloon catheters are manufactured such that axial reduction or shortening is impossible unless the inner catheter shaft buckles, deflecting the tip of the catheter.

With the balloon catheter according to the present invention, the balloon is capable of increased radial expansion into a larger profile than previously possible, without deflecting the tip of the catheter. The novel design of the present invention enables the balloon to shorten longitudinally to facilitate greater expansion of the balloon. A portion of the catheter shaft which is enclosed within the balloon may preferably be constructed to resiliently collapse during inflation of the balloon. This unique arrangement uses an inherent compressive force imposed on the catheter shaft by the sealed ends of the balloon during inflation, coupled with the modified shaft portion of the present invention, to shorten the balloon increase its effectiveness.

The balloon catheter shaft may preferably have a number of elongated openings, extending in a longitudinal direction, arranged in the wall of the portion of the catheter shaft enclosed by the balloon. The remaining circumference of the tubular shaft between these openings then forms at least two strip-shaped members. These strip-shaped members can resiliently bend outwards, such that the enclosed portion can be reduced axially. As a result, the balloon can expand to a greater extent. On supplying inflation fluid under pressure, an axial compressive force is exerted on the enclosed shaft portion due to the radial expansion. The ends of the enclosed shaft portion are then forced towards each other and, as a result of this compressive force, the strip-shaped sections will bend outwards between the openings.

In order to obtain a suitable bending performance, the strip-shaped wall sections preferably bend outwards uniformly around the entire circumference, as a result of which the longitudinal axis of the balloon remains in line with the catheter. The balloon will thus not be pulled out of position upon expansion.

When the balloon is in a deflated state, the strip-shaped members between the openings are longitudinally straight, and they can withstand sufficient compressive force to remain straight when the balloon catheter is introduced into a patient.

According to the preferred embodiment of the present invention, the total axial reduction of the enclosed shaft portion is distributed among different groups of the strip-shaped sections in between each group of openings, so that they are subjected to relatively little outward deformation.

In order to obtain sufficient deformation combined with a suitable stiffness, the cross-section of the strip-shaped sections is preferably flat, so that they bend outwards easily and tend to spring back into their original straight shape.

The catheter according to the present invention may also be provided with an inner tubular member which extends inside the lumen of the basic body, the intended use of which tubular element may be for supplying contrast medium to the distal end of the catheter or for the use of a guidewire.

By employing the measures according to the invention the balloon member can, in the non-expended state, have a small diameter and can be positioned tightly against the basic body. In the expanded state such a balloon can have a larger effective diameter.

These and various other objects, advantages and features of the invention will become apparent from the following description and claims, when considered in conjunction with the appended drawings.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
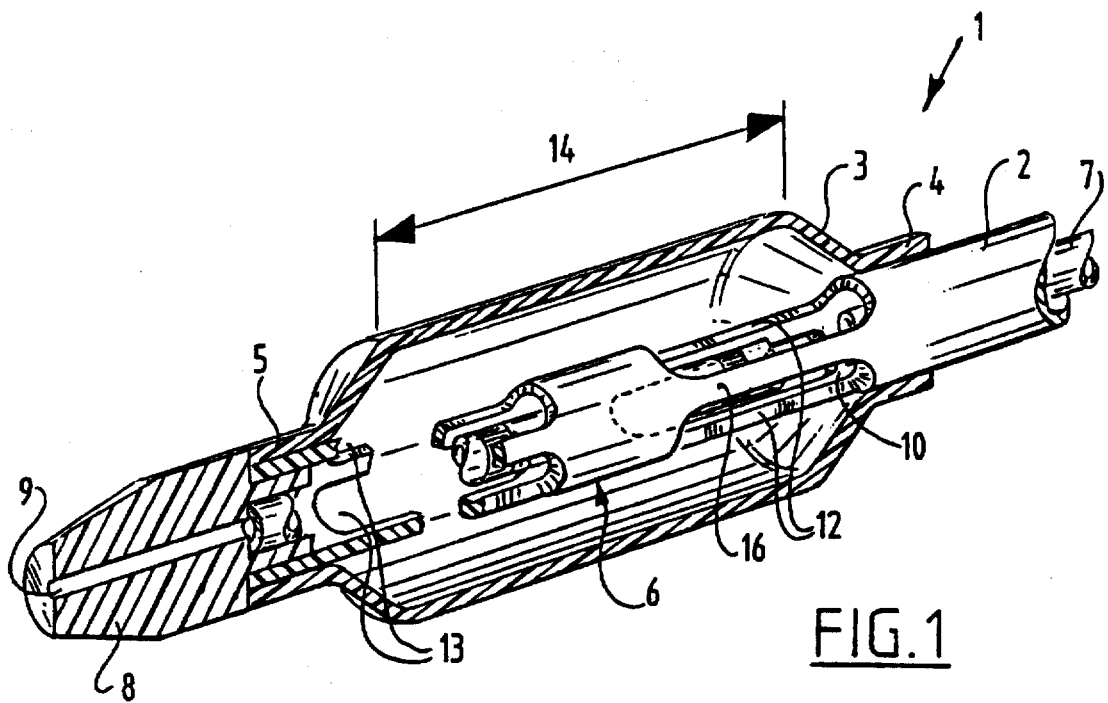
FIG. 1 is a partial perspective cross-sectional view of the balloon catheter arranged according to the principles of the present invention, with the balloon member in a non-expanded state.

With reference to the drawings, the distal end-section of a catheter 1 illustrated in FIG. 1 shows the catheter shaft or basic body 2 of a catheter on which a balloon 3 has been arranged. At the proximal and distal ends 4 and 5 of the balloon 3, the balloon member 3 has been connected with the basic body 2 in a sealed manner. The distal end 5 of the balloon 3 is connected with a separate end-section 8 at the same longitudinal position as the distal end of the basic body 2. In this end-section 8, a canal 9 has been formed to which contrast medium can be supplied through a separate inner lumen or tube 7, which has been received in the lumen 10 of the basic body 2. The inner tube 7 is connected with the end-section 8 at the same height as the end 5 of the balloon member 3 and the end of the basic body 2.

As shown in FIG. 3, one embodiment of the balloon catheter 20 of the present invention includes a hug 22 defining an inflation port 24 and a proximal guidewire port 26. Inflation port 24 communicates with an inflation lumen 28, whereby inflation fluid can be selectively injected into, or removed from, a balloon 30. Balloon catheter 20 further defines a guidewire lumen 32 communicating between proximal guidewire port 26 and a distal guidewire port 34, and guidewire lumen 32 is adapted to slidingly receive a removable guidewire 36.

Figure 2:
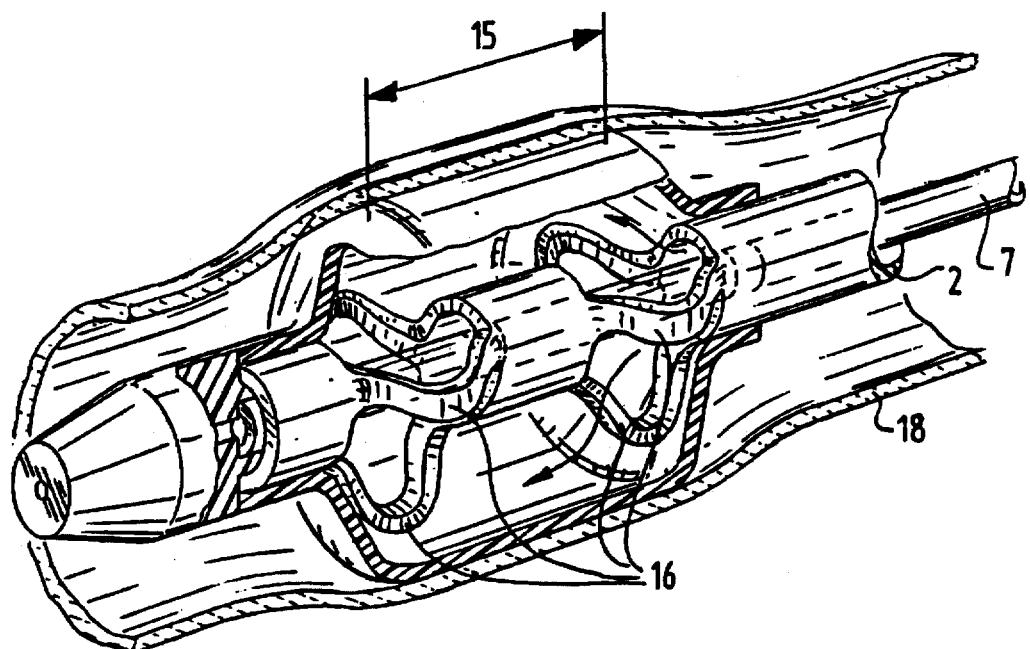
FIG. 2 is a partial perspective cross-sectional view of the balloon catheter of FIG. 1, with the balloon in a fully expanded state.

In the illustrated example of the preferred embodiment, two groups of elongated openings 12 and 13, extending in a longitudinal direction, have been formed in the wall of the enclosed section 6 of the basic body 2 enclosed by the balloon member 3. Each group of openings 12 and 13 respectively have been arranged equally divided around the circumference, preferably over the same longitudinal distance. Several strip-shaped sections 16, which can resiliently bend outwards, are defined in between the openings 12 and 13, as can be seen in FIG. 2. This bending outwards occurs when inflation fluid under pressure is supplied via the lumen 10 of the basic body 2. This inflation fluid flows via the openings 12 and 13 into the balloon member 3 which consequently expands. On expansion, the axial length reduces from the first inflated size indicated with number 14 in FIG. 1 to the greater inflated size indicated with number 15 in FIG. 2. This reduction in length is possible because of the strip-shaped sections bending outwards. As shown in FIG. 2, the longitudinal axis of the catheter shaft distal end tends to remain in its uninflated shape, which is straight in FIG. 2, after inflation.

After the inflation fluid is withdrawn from the balloon 3, the catheter tip will resume the shape shown in FIG. 1 as a result of the elasticity of the strip-shaped sections 16.

The balloon 3 has been made of a relatively inelastic material, so that the shape of the balloon 3 in the expanded state is substantially predetermined. In the non-expanded state, the balloon material is folded in pleats against the basic body 2. This method of folding a balloon is as such known in the art. Because of the size of the openings, the material can be folded in such a way that the non-expanded diameter or deflated profile is relatively small.

It should be understood that an unlimited number of configurations for the present invention can be realized. The foregoing discussion describes merely exemplary embodiments of the principles of the present invention. Those skilled in the art will readily recognize from the description, claims, and drawings that numerous changes and modifications can be made without departing from the spirit and scope of the invention.

I claim:

1. A balloon catheter for use by a health care professional in performing a medical procedure, comprising:
   a tubular shaft having proximal and distal ends and defining an inflation lumen;
   a substantially inelastic balloon having an initial length and being disposed near said tubular shaft distal end;
   wherein said inflation lumen is in fluid communication with the interior of said balloon to conduct a pressurized fluid into the interior of said balloon to inflate said balloon;
   wherein said tubular shaft defines at least two elongated openings disposed on said shaft member within said balloon, whereby said openings define at least a first and second strip member adapted to collapse and bow outwardly and to longitudinally shorten said shaft member during inflation of said balloon; and
   wherein said balloon is adapted to expand to a first inflated profile while said balloon is said initial length, and is adapted to longitudinally shorten upon inflation, thereby allowing a portion of said balloon to radially expand wider said first inflated profile.

2. The balloon catheter as set forth in claim 1, wherein an interior portion of said tubular shaft is enclosed by the balloon, a proximal and distal end of the balloon being affixed to the tubular shaft, and the balloon is adapted to impart a compressive force at said proximal and distal ends on the interior portion of the tubular shaft as the pressurized fluid inflates the balloon thereby shortening the balloon.

3. The balloon catheter as set forth in claim 2, wherein said shaft member is resilient and tends to lengthen upon reduction of the pressure of said pressurized fluid, urging the balloon to lengthen and thereby reducing the deflated profile of said balloon.

4. The balloon catheter as set forth in claim 1, wherein the openings are arranged in at least two longitudinally separated groups, wherein a portion of said shaft member between said groups is free of said openings.

5. The balloon catheter as set forth in claim 4, wherein each opening is longer than the portion of said shaft member between said groups.

6. The balloon catheter as set forth in claim 1, further comprising a guidewire lumen defined by said tubular shaft adapted to slidingly receive a guidewire.

7. The balloon catheter as set forth in claim 1, wherein said at least two openings are longitudinally coextensive and are equally divided around an outer surface of said shaft member.

8. A medical catheter for performing angioplasty with a balloon having increased radial expansion to provide a larger effective inflated profile,
while exhibiting a relatively small deflated profile adapted for percutaneous insertion, comprising:
a balloon catheter adapted to be inserted within the vasculature of a patient, said catheter defining an inflation lumen and a guidewire lumen, said balloon catheter having proximal and distal ends, a substantially inelastic balloon disposed near said distal end, a shaft member extending through said balloon, and an outer shaft surrounding said shaft member, the outer shaft member being sealed to a proximal and distal end of the balloon, said inflation lumen being defined by an annular space between said outer shaft and said shaft member, and communicating with an interior of the balloon to conduct a pressurized fluid from outside the patient into the interior of the balloon, thereby to inflate the balloon from a deflated profile to an inflated profile;
wherein the balloon is adapted to expand to a first inflated shape when the balloon is an initial length, and to impart a compressive force on the outer shaft member at the proximal and distal ends of the balloon sealed to the outer shaft member as the pressurized fluid inflates the balloon; and
wherein the outer shaft member is adapted to collapse and shorten upon inflation of the balloon, thereby shortening the balloon and allowing a portion of said balloon to expand wider than said first inflated shape.

9. The balloon catheter as set forth in claim 8, wherein said outer shaft member is resilient and tends to lengthen upon reduction of the pressure of said pressurized fluid, urging the balloon to lengthen and thereby reducing the deflated profile of said balloon.

10. A balloon catheter for use by a health care professional in performing a medical procedure, comprising:
a tubular shaft having proximal and distal ends, and an outer shaft surrounding said tubular shaft, an inflation lumen being defined by an annular space between said outer shaft and said shaft member;
a substantially inelastic balloon having an initial length and being disposed near said tubular shaft distal end;
wherein said inflation lumen is in fluid communication with the interior of said balloon and is adapted to conduct a pressurized fluid from said tubular shaft proximal end into an interior of said balloon to inflate said balloon; and
wherein said balloon is adapted to expand to a first inflated profile while said balloon is said initial length, and is adapted to longitudinally shorten upon inflation, thereby allowing a portion of said balloon to radially expand wider said first inflated profile.

11. A method of performing an interventional medical therapy procedure in the body of a patient, comprising the steps of:
a) providing a balloon catheter having a proximal hub coupled with a shaft member and an outer tubular shaft surrounding said shaft member, and a substantially inelastic balloon disposed near a distal end of the tubular shaft, said balloon catheter having an inflation lumen communicating with the balloon being defined by an annular space between said outer tubular shaft and said shaft member;
b) inserting the balloon catheter within the body of said patient;
c) conducting a pressurized fluid from said proximal hub through said inflation lumen into the interior of the balloon;
d) inflating the balloon from a deflated profile to a first inflated profile;
e) causing said balloon to shorten and further expand to a second inflated profile that is wider than said first inflated profile.

12. The method as set forth in claim 11, further comprising the step following said step d) of causing a portion of the outer tubular shaft to bow outwardly and shorten.

13. The method as set forth in claim 12, further comprising the step following said step e) of relieving the pressure of said pressurized fluid and allowing said portion of the outer tubular shaft to resiliently increase in length, thereby lengthening the balloon.

14. The method as set forth in claim 11, whereby said step b) causes a longitudinal axis of said tubular shaft to assume an uninflated shape, and said step d) further comprising the step of maintaining said longitudinal axis in said uninflated shape.

* * * * *